United States Patent [19]

Carroll

[11] 4,410,509
[45] Oct. 18, 1983

[54] SYNTHETIC FLY ATTRACTANTS

[75] Inventor: Felix A. Carroll, Davidson, N.C.

[73] Assignee: Trustees of Davidson College, Davidson, N.C.

[21] Appl. No.: 242,315

[22] Filed: Mar. 10, 1981

[51] Int. Cl.³ .............................................. A01N 25/00
[52] U.S. Cl. ...................................... 424/84; 424/314; 424/320; 424/331; 424/337; 424/342
[58] Field of Search ........................................... 424/84

[56] References Cited
PUBLICATIONS

Carroll et al., J. Agric. Food Chem., vol. 28, pp. 343–346, (1980).

Primary Examiner—Leonard Schenkman

[57] ABSTRACT

Synthetic organic compounds that have certain functional groups incorporated into a 23-atom chain are useful as fly attractants. Novel compounds have the general formula

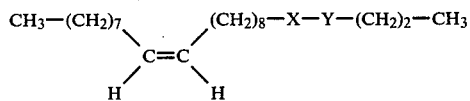

where X is —S—, —O—, or —NH—; and where Y is —CH$_2$— or

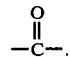

7 Claims, No Drawings

SYNTHETIC FLY ATTRACTANTS

BACKGROUND OF THE INVENTION

This invention relates to the synthesis and use of certain compounds as fly attractants. The compounds may be substituted with acceptable attraction qualities for known compounds which require expensive and complicated synthesis.

The compound cis-9-tricosene was reported by Carlson et al. (Science, volume 174, page 76 (1971)) to be an effective attractant for male houseflies. Carlson et al. synthesized the compound by a Wittig reaction of nonanal with the product of phenyllithium and tetradecyltriphenylphosphonium bromide. The trans isomer of cis-9-tricosene was a minor byproduct of the synthesis. Carlson and Beroza (Environmental Entomol., Volume 2, page 555 (1979)) showed that the cis compound could attract male and female houseflies to sticky traps or poison-baited food traps in field tests and thus could be used as an aid in controlling fly populations. Carlson et al. (J. Agr. Food Chem., Volume 22, page 194 (1974)) showed that hydrocarbon analogs of cis-9-tricosene which had longer or shorter carbon skeltons were not as effective at attracting flies.

Other syntheses of cis-9-tricosene have been reported. Cargill and Rosenblum (J. Org. Chem., Volume 37, page 3971 (1972); U.S. Pat. No. 3,798,273) reported a synthesis by reaction of erucic acid with methyllithium, followed by Wolff-Kishner reduction. Ho and Wong (Can. J. Chem., Volume 52, page 1923 (1974)) have also reported a synthesis involving an olefinic acid and an organolithium compound, as well as by a procedure involving a Grignard reagent and an olefinic acid chloride. An electrolytic procedure has been used by Gribble et al. (J. Chem. Soc. Chem. Commun., page 735 (1973)) and by Meresz and Mosgai et al. (Can. Entomol., Volume 104, page 1963 (1972); U.S. Pat. No. 4,018,844).

All of the previous procedures for synthetic fly attractant synthesis have one or more of the following requirements which add to the cost or difficulty of synthesis: inert atmospheres, anhydrous solvents, organometallic reagents, electrolytic conditions, or contamination by byproducts. Therefore, the need exists for the synthesis of novel compounds which avoid complicated synthesizing requirements but retain acceptable fly attractant qualities.

OBJECTS OF THE INVENTION

It is an object of the present invention to create novel organic compounds that are useful as fly attractants and that can be synthesized easily and economically, without recourse to the conditions listed above.

It is another object of the present invention to employ a number of compounds, some of which are novel, to serve as fly attractants, the compounds differing from the prior art in that they are not hydrocarbons.

These and other objects of the present invention, which will become more apparent as the description of the invention proceeds, are achieved by: a composition of matter, comprising: a compound having the following formula:

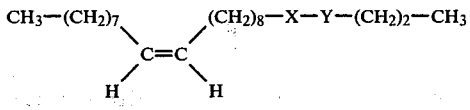

where X is selected from the group consisting of —S—, —O—, or —NH—; and where Y is selected from the group consisting of —CH$_2$— or

These objects are also achieved by: a method to attract flies to fly traps, comprising: applying a fly attractant composition to a fly trap, said fly attractant composition being any non-hydrocarbon chemical compound having 23 atoms in a continuous chain with one cis carbon-carbon double bond in the 9 position from the hydrocarbon terminus in the nonfunctionalized segment of the chain, and further having one or more functional carbonyl or heteroatomic groups in the backbone after a carbon atom in the 17 position from the hydrocarbon terminus in the nonfunctionalized segment of the compound.

DETAILED DESCRIPTION OF THE INVENTION

The fly attractants of the present invention may be characterized as any non-hydrocarbon chemical compound having 23 atoms in a continuous chain with one cis carbon-carbon double bond in the 9 position from the hydrocarbon terminus in the nonfunctionalized segment of the chain, and further having one or more functional carbonyl or heteroatomic groups in the backbone after a carbon atom in the 17 position from the hydrocarbon terminus in the nonfunctionalized segment of the compound. These non-hydrocarbon chemical compounds can function as fly attractants because the sensitivity of fly receptors is not sufficiently refined to fully discriminate against substitution of carbonyl or heteroatomic functional groups with van der Waals radii similar to —CH$_2$— groups and because the non-hydrocarbon compounds are cost effective to synthesize.

Particularly, non-hydrocarbon chemical compounds having the following formula are effective fly attractant compounds:

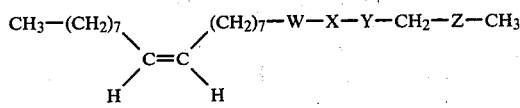

where W is selected from the group consisting of —CH$_2$— and

where X is selected from the group consisting of —S—, —O—, —NH—, and —CH$_2$—; where Y is selected from the group consisting of —CH$_2$— and

when W is —CH$_2$—; where Y is —CH$_2$— when W is

where Z is —CH$_2$— when X is selected from the group consisting of —S—, —O—, and —NH—; where Z is

when W is —CH$_2$—, when X is —CH$_2$—, and when Y is —CH$_2$—; and where Z is —CH$_2$— when W is

Preferred compounds of this formula are found in Table 1.

TABLE 1

| | W | X | Y | Z |
|---|---|---|---|---|
| 1 | —CH$_2$— | —S— | —CH$_2$— | —CH$_2$— |
| 2 | —CH$_2$— | —O— | —CH$_2$— | —CH$_2$— |
| 3 | —CH$_2$— | —O— | $-\overset{\overset{O}{\|}}{C}-$ | —CH$_2$— |
| 4 | —CH$_2$— | —NH— | $-\overset{\overset{O}{\|}}{C}-$ | —CH$_2$— |
| 5 | $-\overset{\overset{O}{\|}}{C}-$ | —NH— | —CH$_2$— | —CH$_2$— |
| 6 | —CH$_2$— | —CH$_2$— | —CH$_2$— | $-\overset{\overset{O}{\|}}{C}-$ |

All of these compounds are different from the prior art in that they are fly attractants that are not hydrocarbons. The compounds 1-5 may be synthesized from smaller organic molecules without reactions that create new carbon-carbon bonds. Synthesis of novel compounds 1-4 is described below. Synthesis of compound 5 is found by reference to E. T. Roe, et. al., J. Amer. Chem. Soc., Volume 71, p. 2215 (1949), except that as practiced herein the reaction solvent is pyridine. Synthesis of compound 6 is described in J. Agric. Food Chem., Vol. 28, pp. 343-346 (1980), which is incorporated by reference as if fully rewritten herein, an article by the inventor and others.

As is shown in Table 2 in Example 5, these compounds increase the number of flies caught by sticky traps. Commercial cis-9-tricosene had an activity of 4.2 in our tests; that is to say, one baited strip caught as many flies as 4.2 unbaited strips in similar locations would have caught. However, the amount of cis-9-tricosene used to bait the strip costs more than three additional strips, so there is no economic advantage to using the attractant chemical. None of the attractants in this invention are quite as active in cis-9-tricosene itself, but they are so much easier to synthesize and would be cheaper. Therefore, the object of the invention is satisfied by economical and uncomplicated synthesis of compounds which may be used to increase the activity of fly traps.

The invention is further described in the following examples.

EXAMPLE 1

Synthesis of Butyl Oleyl Sulfide (1)

Sodium (1.5 g, 0.05 mol) was added to n-butyl mercaptan (9.02 g, 0.10 mol, Eastman) in a dry three-necked, 250-mL, round-bottom flask equipped with drying tube, magnetic stirrer, stopper, and nitrogen inlet. The reaction mixture was cooled in an ice bath. As the reaction progressed, the mixture began to solidify, so sufficient (ca. 5 mL) mixed xylene was added to effect solution. At the end of 6 hr. evolution of hydrogen was no longer apparent. Oleyl tosylate (16.94 g, 0.04 mol) was added to the solution with stirring. The flask was packed in ice and allowed to warm over 15 hr. The reaction mixture was dissolved in ether and extracted with water, 10% NaHCO$_3$, and saturated NaCl. The ether phase was dried over anhydrous potassium carbonate and filtered, and the ether was removed on a rotary evaporator. Vacuum distillation [165° C. (0.5 torr)-190° C. (0.65 torr)] produced an oil with a faint yellow color and an odor characteristic of mercaptans. Lithium aluminum hydride was added to the oil and it was allowed to sit overnight, then filtered, and redistilled. The product was a faintly yellow oil with a slight mercaptan odor. The yield was 6.6 g (48.4%) collected from 212° C. (2.8 torr) to 223° C. (2.7 torr): NMR δ 0.9-2.3 (m, 38 H, —CH$_3$ and —CH$_2$—), 2.5 (m, 4 H, —CH$_2$—S), 5.3 (t, J=4.5 Hz, 2 H, olefinic); IR: 3005 cm$^{-1}$ (olefinic C—H). Anal. Calcd.: C, 77.57; H, 13.02; S, 9.41. Found: C, 77.53; H, 13.02; S, 9.40.

EXAMPLE 2

Synthesis of Butyl Oleyl Ether (2)

Sodium (2.33 g, 0.10 mol) was placed in a three-necked, 250-mL round-bottom flask equipped with nitrogen inlet, mechanical stirrer and drying tube, and 1-butanol (36.6 mL, 0.4 mol) was added to the flask. The reaction mixture was left in a hood overnight, by which time evolution of hydrogen had ceased and all of the sodium appeared to have reacted. Oleyl tosylate (17 g, 0.04 mol, made from oleyl alcohol and tosyl chloride) dissolved in 1-butanol (9.15 mL, 0.1 mol) was added. The solution, which began to turn yellow immediately, was packed in ice and allowed to warm to room temperature over 15 hr. The reaction mixture was washed with water. The organic phase was dissolved in ether and extracted with 10% Na$_2$CO$_3$ and with saturated NaCl. The ether phase was dried over anhydrous potassium carbonate and filtered, and the solvent was removed on a rotary evaporator. The resulting pale-orange oil was distilled (155-168° C. at 0.6 torr) to yield 8.2 g (64%) of 2 as an oil: NMR δ 0.9-2.2 (m, 38 H, —CH$_3$ and —CH$_2$—), 3.2 (t, J=6 Hz, 4 H, —CH$_2$—O), 5.28 (t, J=4.5 Hz, 2 H, olefinic); IR:3010 (olefinic C—H), 1120 cm$^{-1}$ (C—O). Anal. Calcd.: C, 81,41; H, 13.66. Found: C, 81.44; H, 13.68.

EXAMPLE 3

Synthesis of Oleyl Butyrate (3)

Oleyl alcohol (40 g, Eastman) and anhydrous pyridine (10 ml) were added to a 100 ml round-bottom flask equipped with a magnetic stirrer. The mixture was stirred and cooled in an ice bath for five minutes. Butyryl chloride (15.0 g, 0.14 mol, Eastman) was added dropwise via an addition funnel. The reaction mixture was stirred for 15 minutes at 5° and at room temperature for an hour. It was then diluted with ether and filtered. The filtrate was dried over sodium sulfate. Volatiles were removed under vacuum. Distillation of the residual oil (163°–168°, 0.26–0.28 torr) gave 16.2 g (34%) of 3. NMR: $\delta$ 0.9 (m, 6 H, CH$_3$), 1.1–2.4 (m, 32 H, CH$_2$), 3.95 (t, J=6 Hz, CH$_2$O), 5.3 (t, J=4.5 Hz, 2 H vinyl). IR: 3005 (olefinic-CH), 1740 (C=O), 1175 cm$^{-1}$ (C—O—C)

EXAMPLE 4

Synthesis of N-oleylbutyramide (4)

Oleylamine (80.0 g, 0.3 mol, Pfaltz and Bauer) and anhydrous pyridene (20 ml) were added to a 250 ml three-necked round-bottom flask equipped as above. The mixture was warmed until it was homogenous, then cooled to 5° C. Bytyryl chloride (30.0 g, 0.28 mol, Eastman) was added dropwise. The reaction temperature rose rapidly and the mixture solidified. Ether (50 ml) was added, and the resulting solution was stirred overnight at room temperature. The reaction mixture was taken up in ether and washed with water (3×), 10% HCl (4×), 10% Na$_2$CO$_3$ (3×), and saturated NaCl (3×). Drying and removal of the organic phase under vacuum left the crude 4. It was distilled (211°/0.9 torr to 238°/0.25 torr) to yield 40.9 g (43%) of a yellow-white waxy solid which liquified at 37.0°–38.5° C. IR: 3300 (N—H), 3005 (vinyl C—H), 1640 (C=O), 1550 (N—H) cm$^{-1}$.

EXAMPLE 5

Field Testing Procedures

The field test procedure was similar to a method reported by Carlson and Beroza (1973). Commercial (Aeroxon) adhesive-coated paper strips (4×300 cm) were used as fly traps. The attractant (50±5 mg) was dissolved in 0.5 mL of hexane in a vial. About 1 mL of ground corn cobs sifted through wire mesh was added to the solution, and the solvent was allowed to evaporate overnight. The resulting 1 mL of ground cobs was sprinkled over the adhesive strip at the field site. Ground cobs treated only with hexane sprinkled on other adhesive strips served as controls.

The test site was a horse stable near Huntersville, N.C. Four stalls of equal size opened to the outside on the east and west sides of the 13×12 meter structure. These stalls were protected by a roof extending 2 meters beyond each side of the stable. The test strips were hung vertically from the roof beams and were about 2.5 meters above the ground and 0.5 meters from the outer wall of the stable. Eight testing sites, four on each side of the stable, were selected so that each was directly in front of a stall. The baited and unbaited (control) strips were hung 1.3 meters apart. The baited strips were at least 2 meters apart. The compounds were initially assigned test positions at random, but almost all of the compounds were tested in all eight locations. Four compounds were tested on each side of the stable each day. Test strips were installed about 9:00 a.m. and retrieved at the same time the following day. The relative attractant power of a strip was taken as the number of flies caught by a baited strip in a 24-hour period divided by the average number of flies caught by all the unbaited strips on that side of the stable during the same 24-hour period.

The results of the tests are shown in Table 2. As may be seen, novel compound 1 provides acceptable activity with 80% better activity than a control strip. Further, new use of compound 6 as a fly attractant provides acceptable activity with 100% better activity than a control strip.

TABLE 2

| Compound No. | Name | Activity |
|---|---|---|
| — | Commercial (Aldrich) cis-9-tricosene | 4.2 |
| 1 | Butyl Oleyl Sulfide | 1.8 |
| 2 | Butyl Oleyl Ether | 1.1 |
| 3 | Oleyl Butyrate | 1.2 |
| 4 | N—Oleylbutyramide | 1.1 |
| 5 | N—Butyloleamide | 1.3 |
| 6 | cis-14-tricosen-2-one | 2.0 |

While according to the Patent Statutes, preferred embodiments of the invention have been disclosed, the invention is not to be limited thereto or thereby. Consequently, for an understanding of the scope of the invention, reference is made to the following claims.

I claim:

1. A method to attract flies to fly traps, which comprises placing a concentration of about 50 milligrams of a fly attractant chemical compound per about 1200 square centimeters of trap surface area on the fly trap and wherein said fly attractant chemical compound has the following formula:

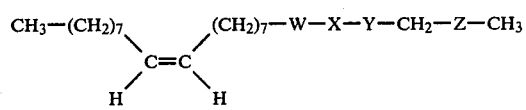

where W is selected from the group consisting of —CH$_2$— and

where X is selected from the group consisting of —S—, —O—, —NH—, and —CH$_2$—;
where Y is selected from the group consisting of —CH$_2$— and

when W is —CH$_2$—;
where Y is —CH$_2$— when W is

where Z is —CH$_2$— when X is selected from the group consisting of —S—, —O—, and —NH—; where Z is

when W is —CH$_2$—, when X is —CH$_2$—, and when Y is —CH$_2$—; and where Z is —CH$_2$— when W is

2. A method to attract flies according to claim 1, wherein W is —CH$_2$— and X is —S— and Y is —CH$_2$— and Z is —CH$_2$—.

3. A method to attract flies according to claim 1, wherein W is —CH$_2$— and X is —O— and Y is —CH$_2$— and Z is —CH$_2$—.

4. A method to attract flies according to claim 1, wherein W is —CH$_2$— and X is —O— and Y is

and Z is —CH$_2$—.

5. A method to attract flies according to claim 1, wherein W is —CH$_2$— and X is —NH— and Y is

and Z is —CH$_2$—.

6. A method to attract flies according to claim 1, wherein W is

and X is —NH— and Y is —CH$_2$— and Z is —CH$_2$—.

7. A method to attract flies according to claim 1, wherein W is —CH$_2$— and X is —CH$_2$— and Y is —CH$_2$— and Z is

* * * * *